(12) United States Patent
Lee et al.

(10) Patent No.: US 8,322,334 B2
(45) Date of Patent: Dec. 4, 2012

(54) NEBULIZER

(75) Inventors: Gary C. J. Lee, I-Lan (TW); Yu-Chien Yen, I-Lan (TW); Thomas Loescher, Carlsbad, CA (US)

(73) Assignee: Galemed Corporation, I-lan (TW)

( * ) Notice: Subject to any disclaimer, the term of this patent is extended or adjusted under 35 U.S.C. 154(b) by 308 days.

(21) Appl. No.: 12/586,180

(22) Filed: Sep. 17, 2009

(65) Prior Publication Data

US 2010/0206305 A1    Aug. 19, 2010

(30) Foreign Application Priority Data

Feb. 19, 2009 (TW) .............................. 98105273 A (51) Int. Cl.
*A61M 11/00* (2006.01)
*A61M 11/02* (2006.01)
*A61M 11/06* (2006.01)
(52) U.S. Cl. ......... 128/200.21; 128/200.11; 128/200.14; 128/203.12; 128/204.14; 128/204.18; 239/338
(58) Field of Classification Search ............. 128/200.11, 128/200.14, 200.18, 200.21, 201.21, 202.27, 128/203.12, 204.14, 204.18, 204.24, 204.25, 128/912; 239/338
See application file for complete search history.

(56) References Cited

U.S. PATENT DOCUMENTS

| 3,744,722 A * | 7/1973 | Burns ........................... 239/338 |
| 3,744,771 A * | 7/1973 | Deaton ......................... 261/78.2 |
| 4,767,576 A * | 8/1988 | Bagwell .......................... 261/16 |
| 4,778,334 A | 10/1988 | Medgyesy et al. |
| 6,328,030 B1 * | 12/2001 | Kidwell et al. .......... 128/200.21 |

FOREIGN PATENT DOCUMENTS

CN        2721119 Y      8/2005

* cited by examiner

*Primary Examiner* — Clinton T Ostrup
(74) *Attorney, Agent, or Firm* — Kilpatrick Townsend & Stockton LLP (57) ABSTRACT

A nebulizer includes a receptacle for containing a liquid, a liquid-drawing tube, and a hollow cover including a partition plate dividing an interior of the cover into first and second chambers, first and second conduits each having an inlet end adapted to be connected to a compressed gas supply tube, and an outlet end communicated with the first chamber, and a mist output tube communicating fluidly with the second chamber. A nebulizing unit is connected to the outlet end of the first conduit and the liquid-drawing tube for directing a first compressed gas from the first conduit to the liquid exiting from the tube to convert the liquid into a mist. The second conduit introduces into the first chamber a second compressed gas which entrains the mist when flowing to the second chamber and exiting through the mist output tube.

5 Claims, 7 Drawing Sheets

NEBULIZER

CROSS-REFERENCE TO RELATED APPLICATION

This application claims priority to Taiwanese Application No. 098105273, filed Feb. 19, 2009, the disclosure of which is incorporated herein by reference.

BACKGROUND OF THE INVENTION

1. Field of the Invention

This invention relates to a nebulizer for a nebulizer breathing system.

2. Description of the Related Art

Figure 1:
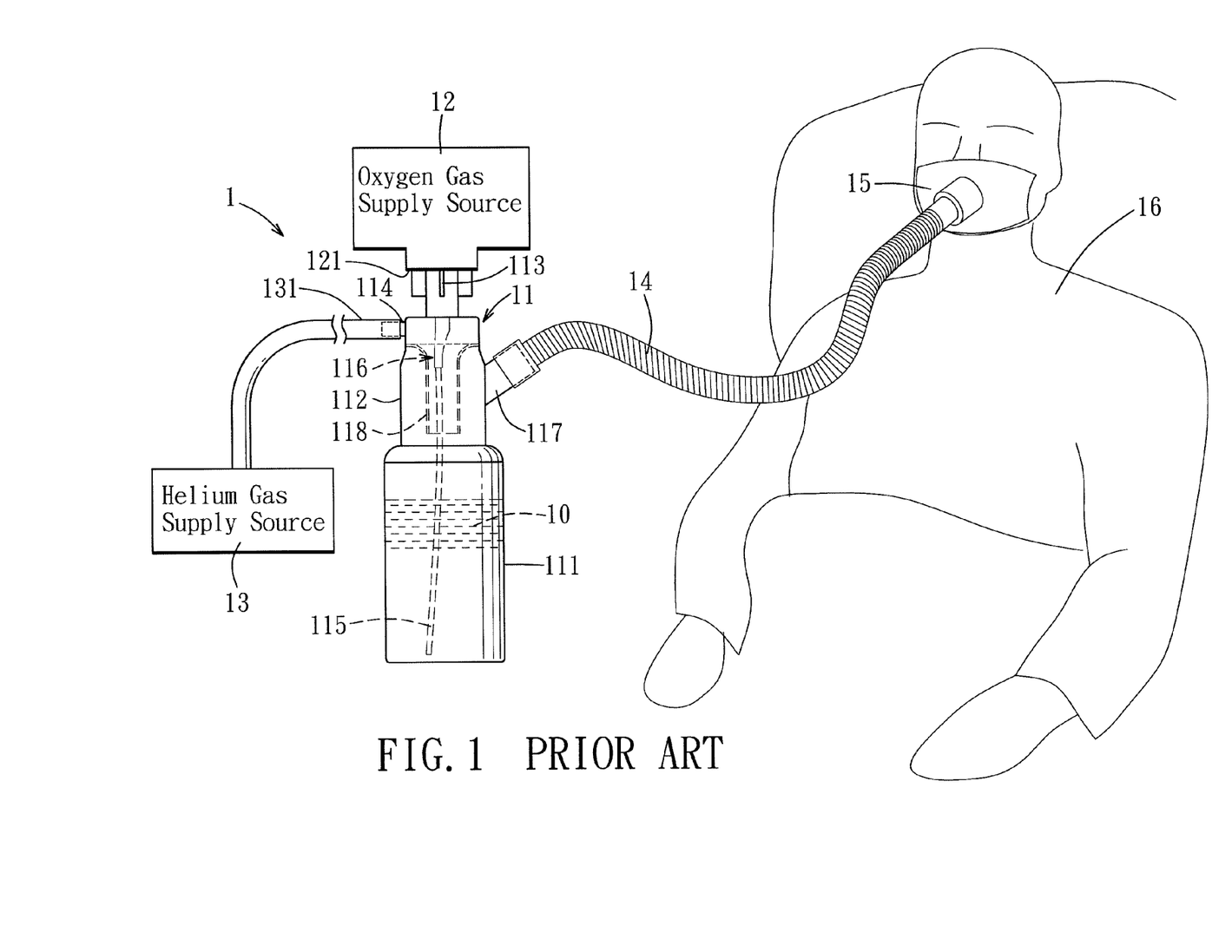
FIG. 1 is a schematic view of a conventional nebulizer breathing system.

Referring to FIG. 1, a conventional nebulizer breathing system 1 includes a nebulizer 11, a delivery tube 14, and a facial mask 15. The nebulizer 11 includes a receptacle 111 containing a liquid medication 10, and a cover 112 connected threadedly to and covering the receptacle 111. A top end of the cover body 112 is provided with an adapter 113 for connection with an outlet 121 of an oxygen gas supply source 12. An inlet tube 114 projects outwardly from a left side of the cover 112 for connection with a supply tube 131 of a helium gas supply source 13, and an outlet tube 117 projects outwardly from a right side of the cover 112. The oxygen gas and helium gas supply sources 12, 13 respectively supply compressed oxygen and helium gases to the nebulizer 11. The delivery tube 14 has one end connected to the outlet tube 117, and the other end connected to the facial mask 15. A liquid-drawing tube 115 in the nebulizer 11 draws the liquid medication 10 upwardly toward the paths of the compressed oxygen and helium gases. Through a nebulizing unit 116, the liquid medication 10 is converted into a mist, and the mist, in turn, is delivered by the compressed oxygen and helium gases into the lungs of a patient 16 through the outlet tube 117, the delivery tube 14, and the facial mask 15.

Although the nebulizer 11 of the conventional nebulizer breathing system 1 can achieve its intended purpose, it has the following drawbacks:

1. The cover 112 is further provided with an inner tube 118 within an interior thereof to guide mixing of the compressed oxygen and helium gases. Since the specific gravity of the helium gas is lighter than that of the oxygen gas, and since the nebulizer 11 is not provided with a blocking plate to alter the flow of the compressed helium gas, the compressed helium gas easily remains at a top portion of the inner tube 118, thereby reducing the amount of the compressed helium gas to be mixed with the mist.

2. Although the inner tube 118 can permit mixing of the compressed gases and the mist, after which the compressed gases and the entrained mist flow out from the outlet tube 117, since the compressed gases carry the mist to flow therealong through a bottom end of the inner tube 118, some of the compressed gases carry the mist to flow to a left, front, or rear side of the inner tube 118, and cannot move the mist directly to a right side of the inner tube 118 toward the outlet tube 117.

3. The compressed gases and the entrained mist must completely fill up the interior of the cover 112 before they can flow out from the outlet tube 117. This results in reducing the efficiency of delivering the mist and in wasting of the mist.

4. Since the inlet tube 114 and the adapter 113 are provided on an outer portion of the cover 112, the size of the nebulizer 11 is increased.

5. To refill the liquid medication 10 inside the receptacle 111, the cover 112 must be threadedly removed first from the receptacle 111. Hence, use of the conventional nebulizer 11 is very inconvenient.

SUMMARY OF THE INVENTION

Therefore, the object of the present invention is to provide a nebulizer for a nebulizer breathing system that is capable of overcoming the aforementioned drawbacks of the prior art.

According to this invention, a nebulizer for a nebulizer breathing system comprises a receptacle, a hollow cover, liquid-drawing tube, and a nebulizing unit. The receptacle defines a storing space for containing a liquid, and has a top open-end portion. The hollow cover has a bottom open-end portion connected to the top open-end portion, and includes a partition plate extending downwardly from a top wall of the cover into the top open-end portion and dividing an interior of the cover into first and second chambers, first and second conduits connected integrally to the top wall in the first chamber, and a mist output tube projecting upwardly from the top wall and communicating fluidly with the second chamber. The first conduit has a first inlet end opening at an outer surface of the cover and adapted to be connected to a first compressed gas supply tube, and a first outlet end communicated with the first chamber. The second conduit has a second inlet end opening at an outer surface of the cover and adapted to be connected to a second compressed gas supply tube, and a second outlet end communicated with the first chamber. The liquid-drawing tube is disposed in the storing space for drawing the liquid, and has an exit end. The nebulizing unit is disposed in the first chamber, and is connected to the first outlet end and the exit end of the liquid-drawing tube for directing a first compressed gas from the first conduit to the liquid exiting from the exit end of the liquid-drawing tube and for converting the liquid into a mist. The second conduit introduces into the first chamber a second compressed gas which entrains the mist when flowing to the second chamber and exiting through the mist output tube.

BRIEF DESCRIPTION OF THE DRAWINGS

Other features and advantages of the present invention will become apparent in the following detailed description of the preferred embodiment of the invention, with reference to the accompanying drawings, in which.

DETAILED DESCRIPTION OF THE PREFERRED EMBODIMENT

Figure 2:
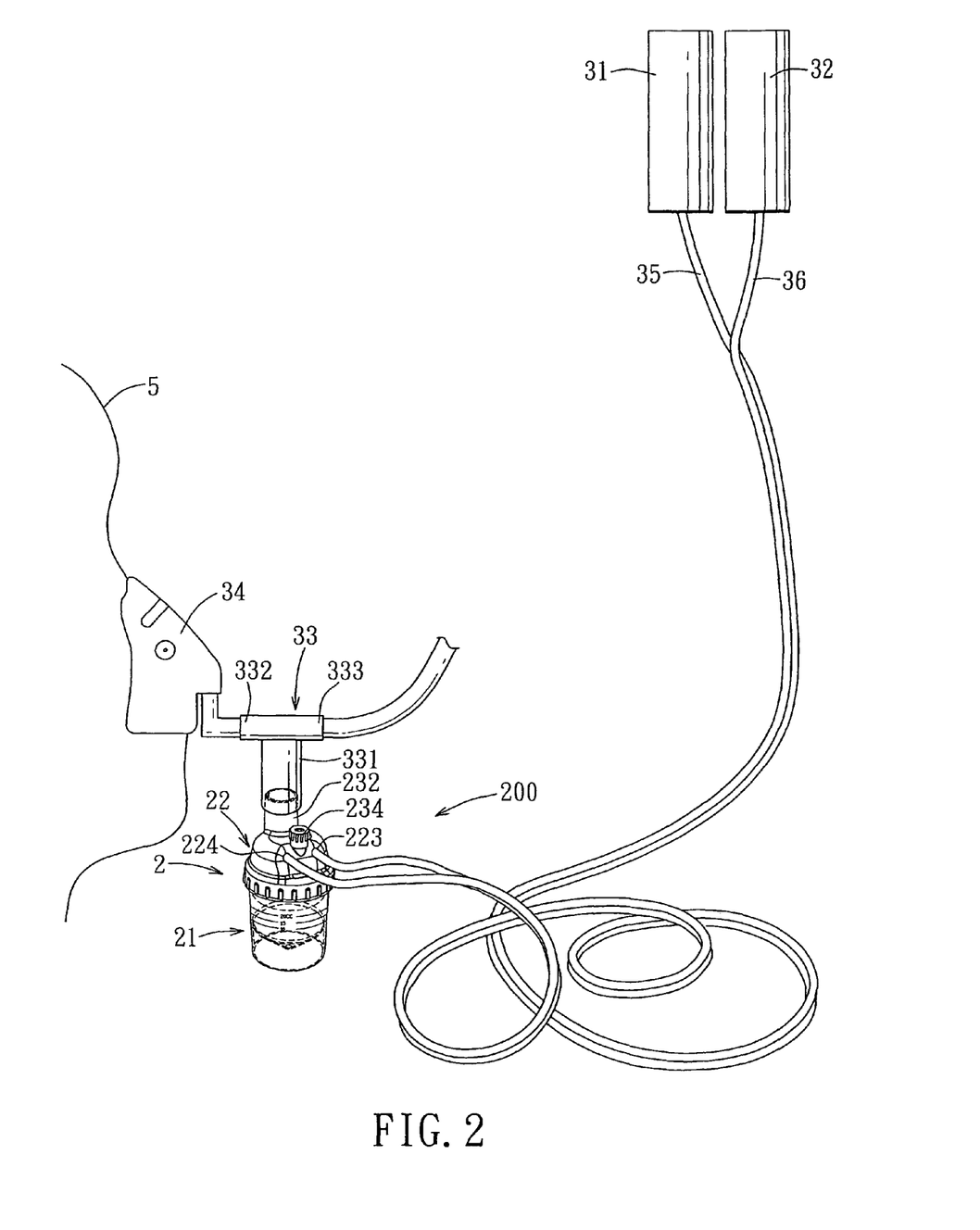
FIG. 2 is a schematic view of a nebulizer breathing system incorporating a nebulizer according to the preferred embodiment of the present invention.
Figure 3:
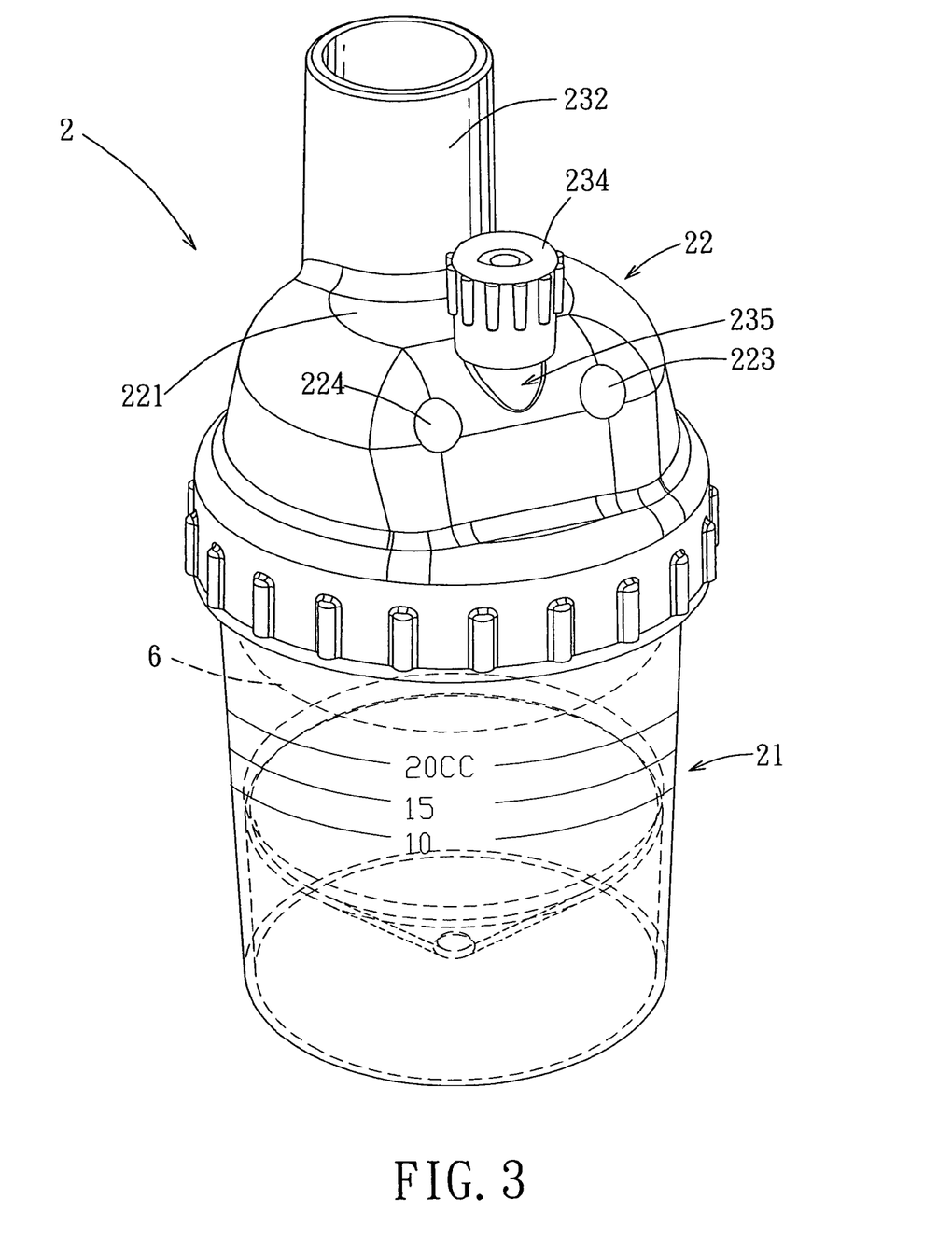
FIG. 3 is a perspective view of the preferred embodiment.

Referring to FIG. 2, a nebulizer 2 according to the preferred embodiment of the present invention is shown adapted to be incorporated in a nebulizer breathing system 200 which includes first and second compressed gas supply sources 31, 32, a T-connector 33, and a facial mask 34. The first compressed gas supply source 31 is connected fluidly to the nebulizer 2 through a first compressed gas supply tube 35 for supply of a first compressed gas to the nebulizer 2. The second compressed gas supply source 32 is connected fluidly to the nebulizer 2 through a second compressed gas supply tube 36 for supply of a second compressed gas to the nebulizer 2. In this embodiment, the first compressed gas supply source 31 supplies a compressed oxygen gas to the nebulizer 2, while the second compressed gas supply source 32 supplies a compressed helium gas to the nebulizer 2. The nebulizer 2 is disposed between the T-connector 33 and the first and second compressed gas supply tubes 35, 36. The T-connector 33 has a first end 331 connected fluidly to the nebulizer 2, a second end 332 connected fluidly to the facial mask 34, and a third end 333 opposite to the second end 332. Through such a connection, a mist produced by the nebulizer 2 can be delivered to the lungs of a patient 5 through the T-connector 33 and the facial mask 34. Further, air exhaled by the patient 5 can be discharged out of the system through the third end 333 of the T-connector 33.

With reference to FIGS. 2 to 7, the nebulizer 2 of the present invention is shown to comprise a receptacle 21, a hollow cover 22, and a nebulizing unit 24. The receptacle 21 defines a storing space 211 for containing a liquid, and has a top open-end portion 210 provided with an external thread 212. In this embodiment, the liquid is a liquid medication 6. In an alternative embodiment, the liquid may be water.

The hollow cover 22 has a bottom open-end portion 220 provided with an internal thread 222 that is connected to the external thread 212 of the receptacle 21. Through such a connection, the cover 22 can engage threadedly and cover the top open-end portion 210 of the receptacle 21. The cover 22 includes a partition plate 225 extending downwardly from a top wall 221 of the cover 22 into the top open-end portion 210 and dividing an interior of the cover 22 into a first chamber 226 and a second chamber 227, first and second conduits 228, 229 connected integrally to the top wall 221 in the first chamber 226, and a mist output tube 232 projecting upwardly from the top wall 221 and communicating fluidly with the second chamber 227.

The first conduit 228, in this embodiment, has a substantially L-shaped cross section, and has a first inlet end 223 opening at an outer surface of the cover 22, a first outlet end 223' communicated with the first chamber 226 and extending downwardly near the partition plate 225, and a gas passage 230 extending from the first inlet end 223 in a direction transverse to the partition plate 225 and thereafter in a downward direction to the first outlet end 223'. The second conduit 229 has a second inlet end 224 opening at an outer surface of the cover 22, a second outlet end 224' opposite to the second first inlet end 224, facing the partition plate 225, and communicated with the first chamber 226, and a gas passage 231 extending from the second inlet end 224 to the second outlet end 224' in a direction transverse to the partition plate 225.

The first compressed gas supply tube 35 is fitted to the first conduit 228 via the first inlet end 223, so that compressed oxygen gas can flow into the first chamber 226 through the first compressed gas flow channel 230. The second compressed gas supply tube 36 is fitted to the second conduit 229 via the second inlet end 224, so that compressed helium gas can flow into the first chamber 226 through the gas passage 231. Since the first and second inlet ends 223, 224 are disposed on the same side of the cover 22, insertion of the first and second compressed gas supply tubes 35, 36 into the respective first and second conduits 228, 229 can be facilitated. Hence, speed and convenience of assembly of the aforesaid components can be enhanced.

Figure 4:
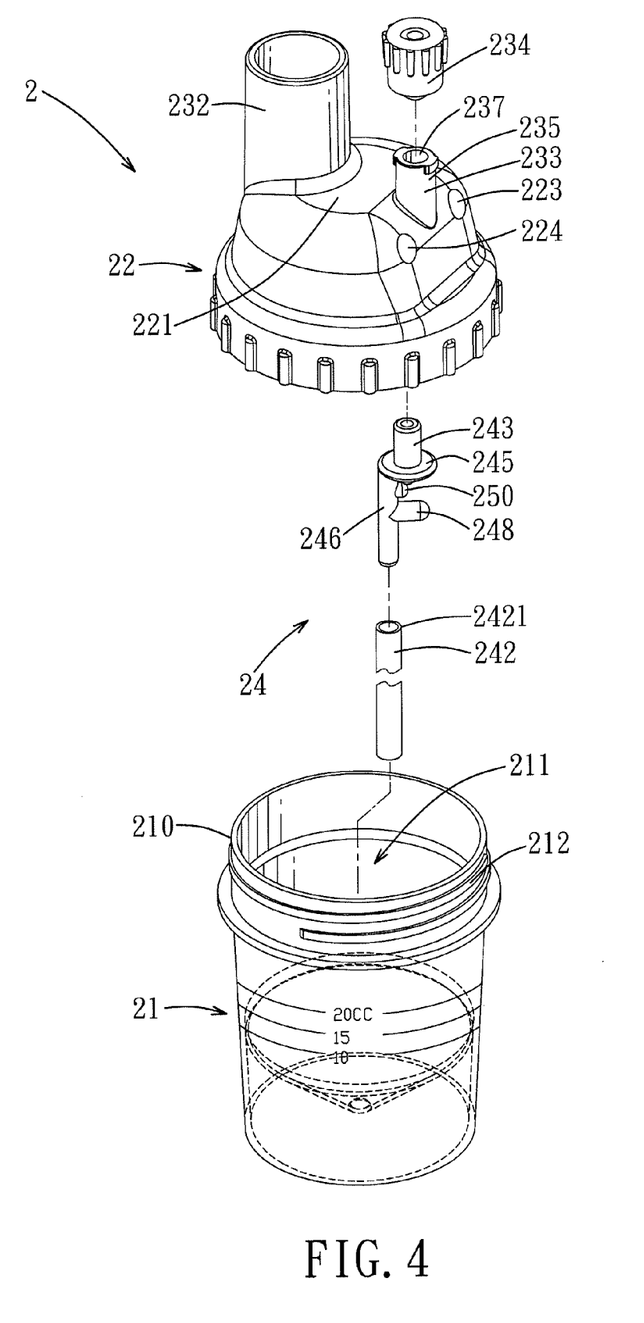
FIG. 4 is an exploded perspective view of the preferred embodiment.
Figure 5:
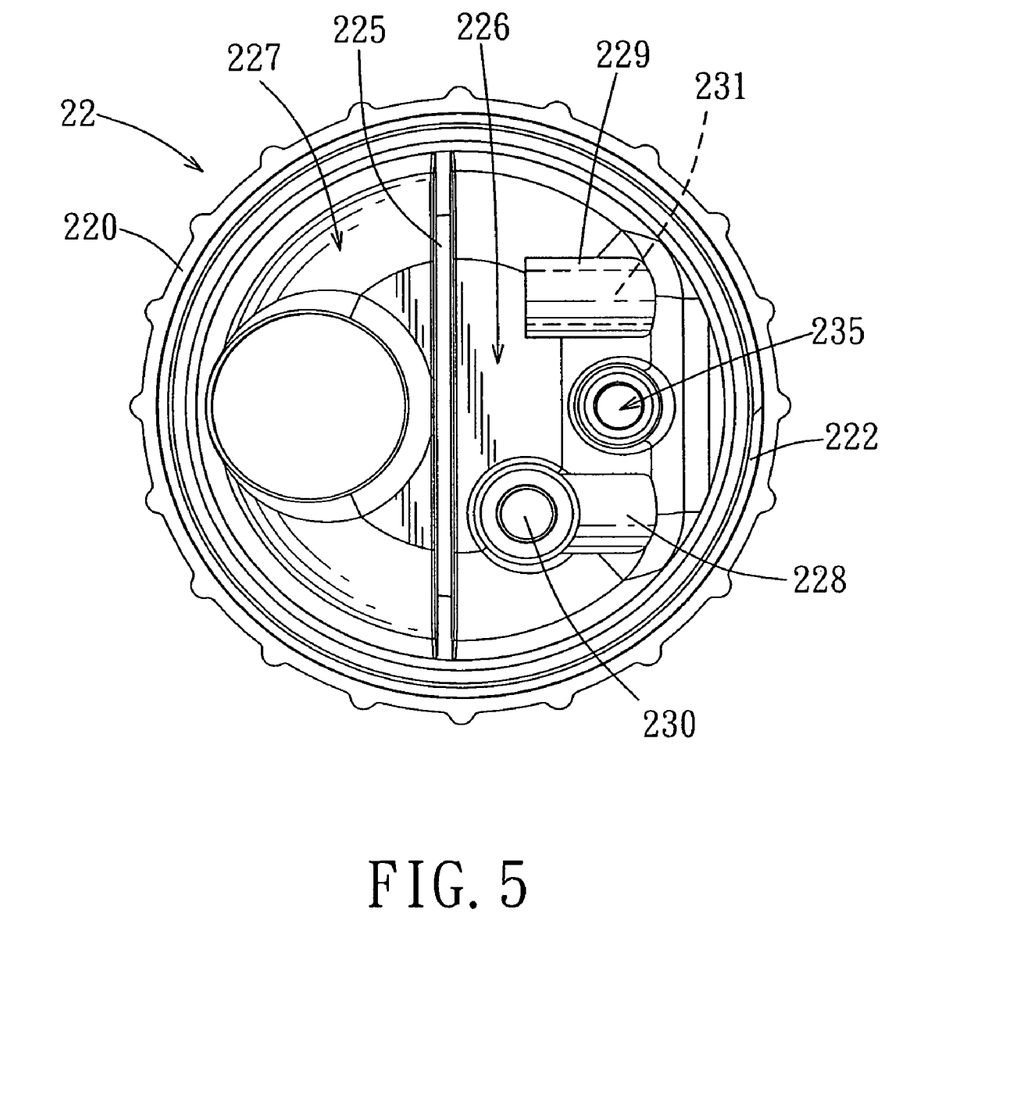
FIG. 5 is a schematic bottom view of a cover of the preferred embodiment.
Figure 6:
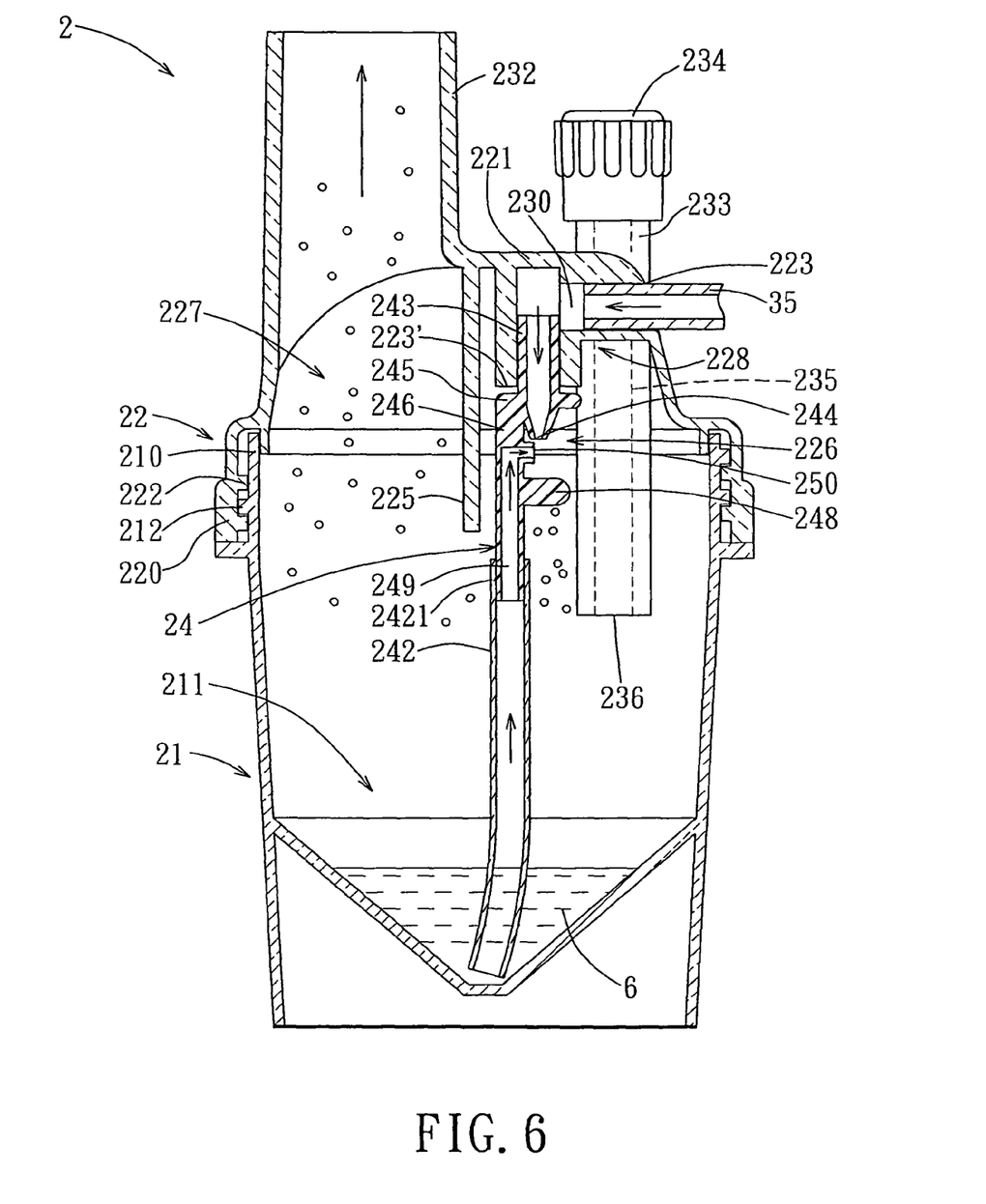
FIG. 6 is a sectional view of the preferred embodiment in an assembled state.
Figure 7:
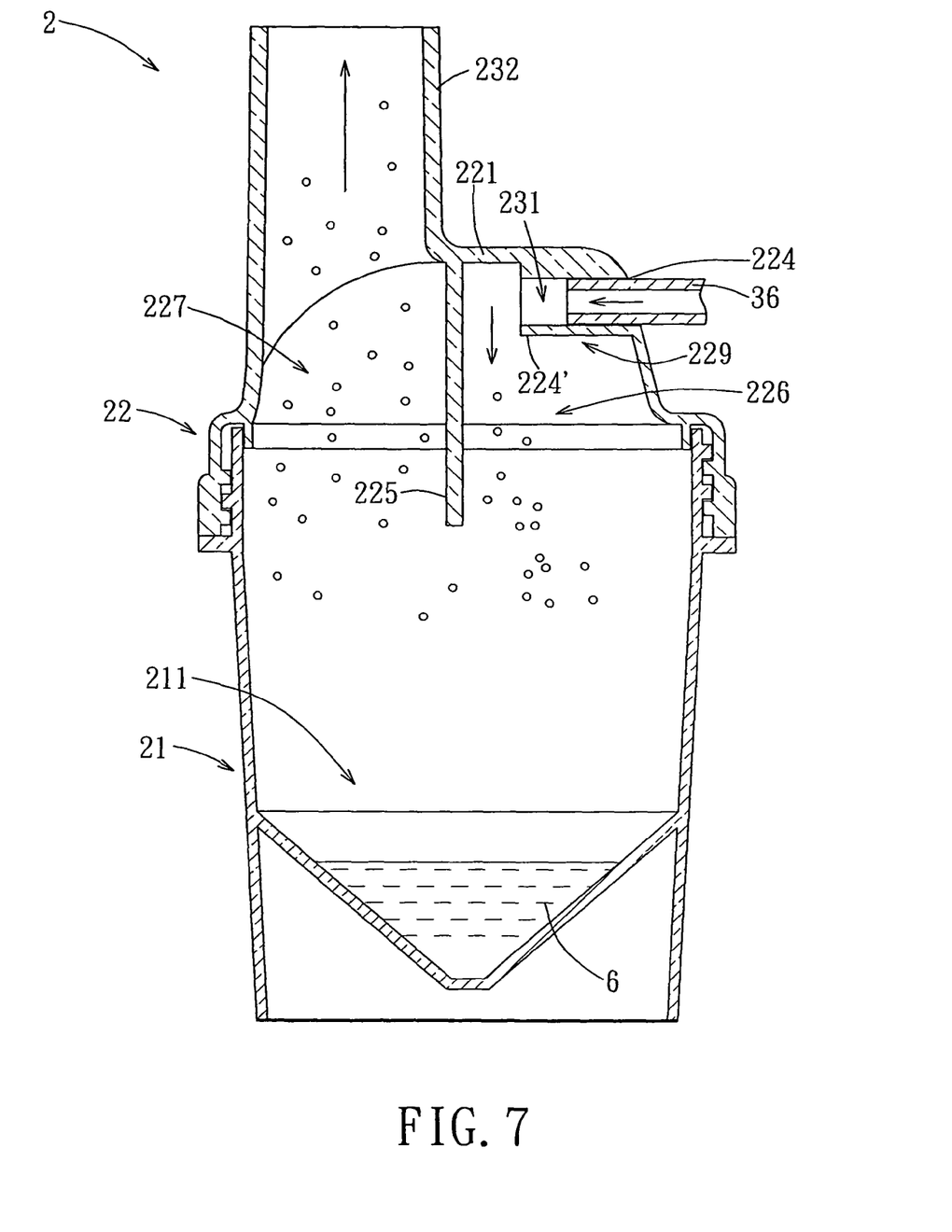
FIG. 7 is another assembled sectional view of the preferred embodiment.

With reference to FIGS. 4, 6, and 7, the nebulizing unit 24 is disposed in the first chamber 226, and includes a gas-flowing tube 243 and a liquid-flowing tube 246. The gas-flowing tube 243 is inserted into the first conduit 228 through the first outlet end 223', and has a gas nozzle 244 for fluid communication of the gas passage 230 and the first chamber 226. An annular limiting flange 245 projects outwardly and radially from an outer surface of the gas-flowing tube 243 for abutment with the first outlet end 223' so as to limit the depth of the gas-flowing tube 243 inserted into the first conduit 228 via the first outlet end 223'. The liquid-flowing tube 246 extends downwardly from the limiting flange 245, defines a liquid passage 249, and has a liquid nozzle 250 integral with and proximate to the gas nozzle 244, and a baffle 248 projecting outwardly and horizontally from one side of the liquid-flowing tube 246 below the liquid and gas nozzles 250, 244. The liquid-drawing tube 242 is disposed in the storing space 211, and has an exit end 2421 connected to a bottom end portion of the liquid-flowing tube 246.

When the compressed oxygen gas flows out from the gas passage 230 through the gas nozzle 244, a negative pressure condition is partially developed below the gas nozzle 244, so that the liquid medication 6 in the receptacle 21 is drawn upwardly through the liquid-drawing tube 242, enters the liquid passage 249, and flows, out via the liquid nozzle 250. Since the flow of the compressed oxygen gas is continuous and is directed toward the liquid medication 6 flowing out from the liquid nozzle 250 through the gas nozzle 244, the liquid medication 6 is carried by the compressed oxygen gas to impact the baffle 248, thereby nebulizing or fracturing the liquid medication 6 into an aerosolized medication or mist.

Since the second outlet end 224' of the second conduit 229 faces the partition plate 225, the compressed helium gas flowing through the gas passage 231 is forced to flow downward. The mist in the first chamber 226 is entrained with the compressed oxygen and helium gases when the gases flow to the second chamber 227, and exit through the mist output tube 232, through the first and second ends 331, 332 of the T-connector 33, through the facial mask 34, and deep into the lungs of the patient 5. It should be noted that by incorporating the helium gas with the oxygen gas, the aerosolized medication or mist can be effectively and accurately administered to the lungs of the patient 5. In an alternative embodiment, the second compressed gas supply tube 36 may be dispensed herewith, so that the mist is delivered through the compressed oxygen gas. However, the delivery effect is not as good as that of the preferred embodiment which makes use of the compressed oxygen and helium gases. Further, the mist output tube 232 may be directly connected to the facial mask 34, and is not limited to the disclosed embodiment. Moreover, through the provision of the partition plate 225 so as to divide the interior of the cover 22 into the first and second chambers 226, 227, the compressed helium gas flowing out from the second outlet end 224' of the second conduit 229 may be redirected so as to flow downward toward a nebulizing area of the nebulizing unit 24. Since the direction of flow of the compressed oxygen and helium gases is similar, when the compressed helium gas is effectively mixed with the mist, the compressed helium and oxygen gases can cooperatively drive the mist to the second chamber 227 and out of the mist output tube 232. Hence, the efficiency of administering the aerosolized medication or mist to the patient 5 is greatly enhanced, and waste of the mist can be minimized, thereby resolving the problems encountered in the aforesaid conventional nebulizer breathing system 1 (see FIG. 1).

The cover 22 further includes a liquid-filling tube 233 and a cap 234. The liquid-filling tube 233 has a top end 235 projecting upwardly from the top wall 221 of the cover 22 and provided with a liquid inlet port 237, and a bottom end 236 extending downwardly into the storing space 211. The cap 234 is connected removably to the top end 235 of the liquid-filling tube 233 so as to cover the liquid inlet port 237 and so as to permit filling and refilling of the liquid medication 6 into the storing space 211 via the liquid inlet port 237. As compared to the aforesaid conventional nebulizer breathing system 1, use of the present invention is very convenient. Further, since the bottom end 236 of the liquid-filling tube 233 is spaced apart from and is disposed below the gas nozzle 244, the liquid medication 6 can flow smoothly into the storing space 211 without being affected by the gas and liquid exiting the gas and liquid nozzles 244, 250.

When the nebulizer 2 of the present invention is assembled on the nebulizer breathing system 200, since the first and second compressed gas supply tubes 35, 36 can be inserted respectively into the first and second inlet ends 223, 224, the nebulizer 2 can be disposed close to the patient 5 so as to prevent the aerosolized medication or mist from remaining in tubes, etc. Further, since the first and second conduits 228, 229 are provided in the interior of the cover 22, the volume of the entire nebulizer 2 can be reduced. Hence, when the nebulizer 2 is used in a small or limited area, such as that for infants, waste of the mist can be effectively minimized, and the delivery effect of the mist can be enhanced.

While the present invention has been described in connection with what is considered the most practical and preferred embodiment, it is understood that this invention is not limited to the disclosed embodiment but is intended to cover various arrangements included within the spirit and scope of the broadest interpretations and equivalent arrangements.

We claim:

1. A nebulizer comprising:
    a receptacle defining a storing space for containing a liquid, and having a top open-end portion;
    a hollow cover having a bottom open-end portion connected to said top open-end portion and including a partition plate extending downwardly from a top wall of said cover into said top open-end portion and dividing an interior of said cover into a first chamber and a second chamber, first and second conduits connected integrally to said top wall within said first chamber, and a mist output tube projecting upwardly from said top wall and communicating fluidly with said second chamber, said first conduit having a first inlet end extending through said top wall to open at an outer surface of said cover and adapted to be connected to a first compressed gas supply tube and a first outlet end communicated with said first chamber, said second conduit having a second inlet end extending through said top wall to open at an outer surface of said cover and adapted to be connected to a second compressed gas supply tube and a second outlet end communicated with said first chamber;
    a liquid-drawing tube disposed in said storing space for drawing the liquid and having an exit end; and
    a nebulizing unit disposed in said first chamber and connected to said first outlet end and said exit end of said liquid-drawing tube for directing a first compressed gas from said first conduit to the liquid exiting from said exit end of said liquid-drawing tube and for converting the liquid into a mist;
    wherein said second conduit introduces into said first chamber a second compressed gas which entrains the mist when flowing to said second chamber and exiting through said mist output tube.

2. The nebulizer of claim 1, wherein said nebulizing unit includes a liquid nozzle connected to said exit end of said liquid-drawing tube, and a gas nozzle connected to said first outlet end, said liquid and gas nozzles being integral with and being proximate to each other.

3. The nebulizer of claim 1, wherein said second conduit further has a gas passage that extends from said second inlet end to said second outlet end in a direction transverse to said partition plate, and said second outlet end faces said partition plate.

4. The nebulizer of claim 3, wherein said first conduit further has a gas passage that extends from said first inlet end in a direction transverse to said partition plate and thereafter in a downward direction to said first outlet end, and said first outlet end extends downwardly near said partition plate.

5. The nebulizer of claim 1, wherein said cover further includes a liquid-filling tube having a top end projecting outwardly from said top wall of said cover, and a bottom end extending downwardly into said storing space, and a cap connected removably to said top end of said liquid-filling tube.

* * * * *